(12) United States Patent
Kwon et al.

(10) Patent No.: US 12,594,386 B2
(45) Date of Patent: Apr. 7, 2026

(54) DRUG VAPORIZATION AND INHALATION DEVICE

(71) Applicant: JD COSPHARMA CO., LTD., Suwon-si (KR)

(72) Inventors: Oh-Seok Kwon, Suwon-si (KR); Min-Ji Kim, Namyangju-si (KR)

( * ) Notice: Subject to any disclaimer, the term of this patent is extended or adjusted under 35 U.S.C. 154(b) by 714 days.

(21) Appl. No.: 17/925,557

(22) PCT Filed: May 12, 2021

(86) PCT No.: PCT/KR2021/005943
§ 371 (c)(1),
(2) Date: Nov. 15, 2022

(87) PCT Pub. No.: WO2021/241921
PCT Pub. Date: Dec. 2, 2021

(65) Prior Publication Data
US 2023/0191044 A1 Jun. 22, 2023

(30) Foreign Application Priority Data
May 28, 2020 (KR) ........................ 10-2020-0064623

(51) Int. Cl.
*A61M 15/00* (2006.01)
*A61M 11/04* (2006.01)

(52) U.S. Cl.
CPC ...... *A61M 15/0006* (2014.02); *A61M 11/042* (2014.02); *A61M 15/0038* (2014.02); *A61M 15/0041* (2014.02); *A61M 2202/064* (2013.01)

(58) Field of Classification Search
CPC ...... A24F 40/30; A61M 11/005; A61M 11/04;

A61M 11/042; A61M 15/00; A61M 15/0003; A61M 15/0006; A61M 15/0024; A61M 15/003; A61M 15/0033; A61M 15/0038; A61M 15/0041; A61M 15/06; A61M 2202/0468; A61M 2202/064; A61M 2205/3653; A61M 2205/3673;

(Continued)

(56) References Cited

U.S. PATENT DOCUMENTS

| | | | |
|---|---|---|---|
| 3,918,451 A | 11/1975 | Steil | |
| 8,464,712 B2 * | 6/2013 | Ganem | ............. A61M 15/0048 |
| | | | 128/203.23 |
| 10,188,585 B1 * | 1/2019 | Busiashvili | ............. A61J 1/201 |

(Continued)

FOREIGN PATENT DOCUMENTS

| | | |
|---|---|---|
| CN | 111182935 A | 5/2020 |
| EP | 1671667 A | 6/2006 |

(Continued)

*Primary Examiner* — Timothy A Stanis
*Assistant Examiner* — Matthew R Moon
(74) *Attorney, Agent, or Firm* — KORUS Patent, LLC; Seong Il Jeong

(57) ABSTRACT

Provided is a drug vaporization and inhalation device. The drug vaporization and inhalation device is configured such that when a user inhales a particulate drug, the drug is contained in vaporized steam, and therefore, the drug can sufficiently arrive at the lungs of the user, without loss, thereby preventing a given amount of the drug from remaining in an inhalation container and improving the drug inhalation efficiency of the user along with prevention of excessive inhalation of the drug.

16 Claims, 8 Drawing Sheets

(58) Field of Classification Search
CPC .... A61M 2205/3686; A61M 2205/583; A61M
2206/16
See application file for complete search history.

(56) References Cited

U.S. PATENT DOCUMENTS

| | | | | |
|---|---|---|---|---|
| 2018/0007974 A1* | 1/2018 | Thorens | .................. | A24F 40/40 |
| 2019/0254344 A1* | 8/2019 | Hepworth | ............. | A61M 15/06 |
| 2021/0235767 A1* | 8/2021 | Akao | .................. | H01M 10/425 |
| 2022/0409831 A1* | 12/2022 | Eliahu | .............. | A61M 15/0041 |

FOREIGN PATENT DOCUMENTS

| | | | |
|---|---|---|---|
| JP | 2011-511674 A | 4/2011 |
| JP | 2015-530214 A | 10/2015 |
| KR | 10-1039837 B1 | 6/2011 |
| KR | 10-2015-0129683 A | 11/2015 |
| KR | 10-2017-0007441 A | 1/2017 |

* cited by examiner

DRUG VAPORIZATION AND INHALATION DEVICE

TECHNICAL FIELD

The present invention relates to a drug vaporization and inhalation device, and more specifically, to a drug vaporization and inhalation device that is capable of allowing a particulate drug to be mixed with vaporized steam and inhaled when an infected patient with asthma, a coronavirus, or the like inhales the particulate drug, so that the drug can sufficiently arrive at the lungs of the infected patient.

BACKGROUND ART

With the development of civilization, generally, modern people suffers from diseases such as asthma, atopy, and the like, that are called "civilizational diseases", owing to various types of pollution and contamination.

So as to solve such problems, many studies on portable inhalers have been made to enhance mental and physical stability, immunity, and health, to replace negative effects of smoking in societies, and to obtain the advantages of aroma or drug everywhere, always, irrespective of time and place.

That is, a drug, which is developed to treat an asthmatic patient or an infected patient with a coronavirus recently emerged to cause great damage all over the world, is made for the purpose of administering a metered aerosol and an inhalant solvent type active compound for the bronchus, and in this case, in specific, the purpose of inhalation powder containing an active material is important in the development of the drug.

In the case of the active material with high effectiveness, a small quantity of active material per single administration is needed so as to achieve the therapeutic effects of the drug. In this case, the active material is diluted with an appropriate excipient to make inhalation powder.

Because of a large quantity of excipient, the characteristics of the inhalation powder are greatly influenced by the excipient selected. When the excipient is selected, the particle sizes of the excipient are very important. The finer the particle sizes are, generally, the worse the low characteristics of the excipient are.

However, if individual capacities of dosage forms are packed and divided, for example, if inhalation capsules (inhalettes) for powder inhalation are made or individual capacities are metered by a patient before he or she uses a multiple administration powder inhaler, excellent flow characteristics are included in conditions required for obtaining high accuracy metering.

Further, the particle sizes of the excipient are very important in the discharge characteristics of the inhalation capsules if the excipient is used for an inhaler. Besides, it is known that the particle sizes of the excipient have important influences on a percentage of an active material of the inhalation powder transferred by means of inhalation. If the active material is inhaled by means of breathing, the percentage of the active material inhaled represents the particles of the inhalation powder moving deeply to the branches of the lungs, and in this case, the sizes of the particles required are in the range of 1 to 10 μm, desirably less than 6 μm.

However, conventional powder inhalers that spray out a powdered drug fail to allow the powdered drug inhaled to sufficiently arrive at a patient's lungs, thereby often causing a given amount of the drug to remain in the inhalers, and accordingly, infected patients with asthma or coronavirus may excessively inhale the drug in consideration of the amount of drug lost.

DISCLOSURE OF THE INVENTION

Technical Problems

Accordingly, the present invention has been made in view of the above-mentioned problems occurring in the related art, and it is an object of the present invention to provide a drug vaporization and inhalation device that is capable of allowing a particulate drug to be mixed with vaporized steam, when an asthmatic patient or an infected patient with a coronavirus recently emerged to generate a great number of patients inhales the particulate drug, so that the drug can sufficiently arrive at the lungs of the infected patient, without loss, thereby preventing a given amount of the drug from remaining in the interior of the device and suppressing excessive inhalation of the drug.

Technical Solutions

To accomplish the above-mentioned objects, according to the present invention, there is provided a drug vaporization and inhalation device including: a vaporization container having a first storage space for storing a vaporization promoting composition and a first guide path for discharging steam; an inducing material disposed under the vaporization container to be inserted into the first storage space to induce the vaporization promoting composition stored in the first storage space to be discharged by means of a capillary action; a fine particle vaporizer heated when power is supplied thereto to vaporize the vaporization promoting composition induced by the inducing material; a body detachably coupled to top of the vaporization container and having a capsule accommodation portion formed on top thereof to accommodate a capsule in which a powdered drug for an infected patient with asthma, a coronavirus, or the like is sealedly stored and second guide paths for steam discharge formed thereon to pass through the interior thereof in an up and down direction thereof, communicate with the first guide path, and discharge the vaporized steam induced from the fine particle vaporizer to the capsule located inside the capsule accommodation portion; and a cap rotatably coupled to top of the body and having a mixing space formed on the inner bottom thereof, an inhalation pipe for the infected patient with asthma, a coronavirus, or the like communicating with the mixing space, and blades protruding downward from the inner bottom thereof to incise the capsule placed in the capsule accommodation portion, so that the vaporized steam or the powdered drug discharged from the capsule and mixed with the vaporized steam guided by the second guide paths is inhaled through the inhalation pipe and reaches the lungs of the infected patient.

According to one aspect of the present invention, the capsule accommodation portion comprises a pair of first wall members for supporting left and right walls of the capsule and a pair of second wall members facingly spaced apart from each other in different directions from the pair of first wall members to support both ends of the capsule, so as to form a space for accommodating the capsule, and blade moving paths formed in spaces between the plate-shaped first wall members and the arch-shaped second wall members to ensure spaces through which the blades pass to incise one surface of the top of the capsule when the cap rotates.

According to another aspect of the present invention, the body, which is coupled to top of the vaporization container, has rail grooves formed on top outer periphery thereof to guide the rotation of the cap and protrusion insertion slots formed on both ends of each rail groove.

According to yet another aspect of the present invention, the blades protrude downward from the inner bottom of the cap, and the cap has locking protrusions formed on the inner periphery thereof, seated on the protrusion insertion slots of the body, and rotating along the rail grooves.

According to still another aspect of the present invention, the body has a first mark formed on the outer peripheral surface corresponding to one protrusion insertion slot and the cap has a second mark formed on the outer peripheral surface corresponding to one locking protrusion, so as to guide a position where the vaporized steam is discharged through the inhalation pipe or a position where the powdered drug discharged from the capsule is mixedly contained in the vaporized steam and thus discharged.

According to another aspect of the present invention, the second guide paths pass through the body in the up and down direction of the body in the form of twisted pipes to thus generate a vortex in the mixing space provided between the cap and the body when the vaporized steam is discharged to the capsule placed between the body and the cap.

According to yet another aspect of the present invention, the second guide paths have "¬"-shaped paths extending from the bottom surface of the body to the inner peripheral surface of the capsule accommodation portion, and the inner outlets of the paths are close to the blade moving paths formed in the spaces between the first wall members and the second wall members.

According to still another aspect of the present invention, each second guide path provides a connection path having a generally "¬"-shaped sectional area by means of a vertical path extending vertically from the bottom of the body and a horizontal path extending horizontally from the vertical path and having an outlet open toward the inner peripheral surface of the capsule accommodation portion.

According to another aspect of the present invention, the horizontal path open toward the inner peripheral surface of the capsule accommodation portion is kept to an inclination of 15 to 45° toward one side of the body from the center of the body, so that the vaporized steam discharged from the second guide paths through the first guide path is positioned toward one side of top of the capsule incised by the blades, and simultaneously, a vortex in the mixing space is generated.

Further, the vaporization container may have a liquid introducing valve for introducing the vaporization promoting composition therethrough.

In addition, the first guide path may be formed definedly at the center of the vaporization container or formed along the inner peripheral surface of the vaporization container.

Moreover, the inducing material may be fixed to a fixing plate having an air inlet hole formed thereon, so that the internal space of the vaporization container or the fine particle vaporizer is divided into an inner space and an outer space.

Further, the inducing material may be made of any one material of a multi-layered foamed nickel wire mesh, a stainless fiber felt, a polymer foaming agent, a metal porous material, and fibers, or a combination thereof.

In addition, the fine particle vaporizer may include: an atomizing container coupled to one end of the vaporization container to accommodate the fixing plate to which inducing material is fixed therein; an electrode part screw-coupled to the inside of the atomizing container; and a heating material disposed on the outside surface of the inducing material accommodated in the atomizing container and thus heated by the power supplied from the electrode part to vaporize the vaporization promoting composition induced by the inducing material.

Moreover, the electrode part may include: an electrode body having an inhalation hole communicating with the first guide path and a coupled screw portion fixed to the bottom inner periphery of the atomizing container whose both ends are open, while being electrically contacted with the atomizing container; a negative electrode disposed on one side of the electrode body to have the electrical contact with the heating material; and a positive electrode disposed on one side of the electrode body to have the electrical contact with the heating material.

Further, the heating material may be a heating filament wire having a coil structure made of a nickel alloy or a composition of rare earth elements, which is connected to the electrodes and wound on the inducing material; a high frequency or very high frequency generator connected to the electrodes so that the inducing material is molded to the shape of a flat plate coming into close contact with the high frequency or very high frequency generator; or comprises peltier elements electrically connected to the electrodes in parallel therewith so that absorber plates of the peltier elements have physical contacts with the heating material; and otherwise, the heating material is a heating filament wire having a coil structure made of a nickel alloy or a composition of rare earth elements, which is connected to the electrodes and wound on the inducing material and a high frequency or very high frequency generator connected to the electrodes, together; or comprises peltier elements electrically connected to the electrodes in parallel therewith so that absorber plates of the peltier elements have physical contacts with the heating material.

Further, the vaporization promoting composition may include any one of a general nutrient, a mineral, a vitamin, an amino acid, and a biostimulant.

Advantageous Effects

According to the present invention, the drug vaporization and inhalation device allows the particulate drug to be mixed with the vaporized steam, when an asthmatic patient or an infected patient with a coronavirus recently emerged to generate a great number of patients inhales the particulate drug, so that the drug can sufficiently arrive at the lungs of the infected patient, without loss, thereby preventing a given amount of the drug from remaining in the interior of the device and suppressing excessive inhalation of the drug.

The effectiveness of the invention is not limited as mentioned above, and it should be understood to those skilled in the art that the effectiveness of the invention may include another effectiveness as not mentioned above from the detailed description of the present invention.

BEST MODE FOR INVENTION

Hereinafter, embodiments of the present invention are disclosed with reference to the attached drawings.

Figure 1:
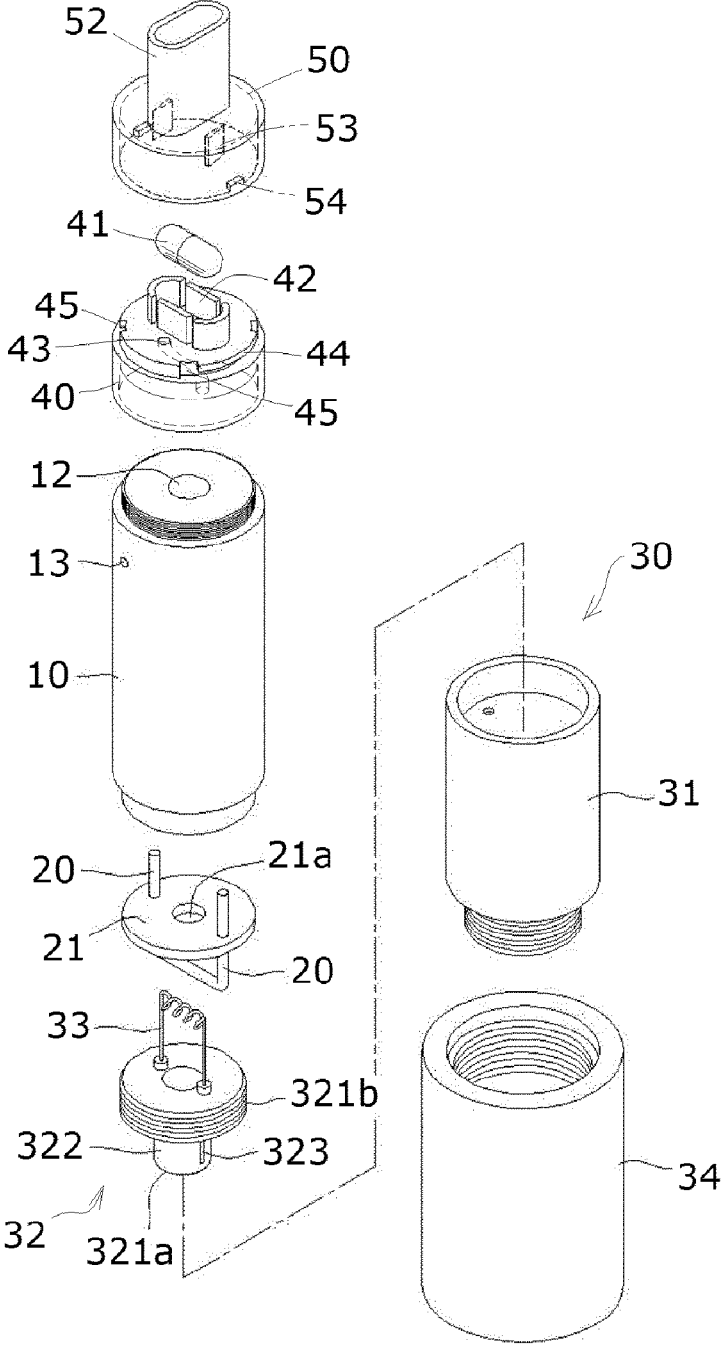
FIG. 1 is an exploded perspective view showing a drug vaporization and inhalation device according to a first embodiment of the present invention.
Figure 2:
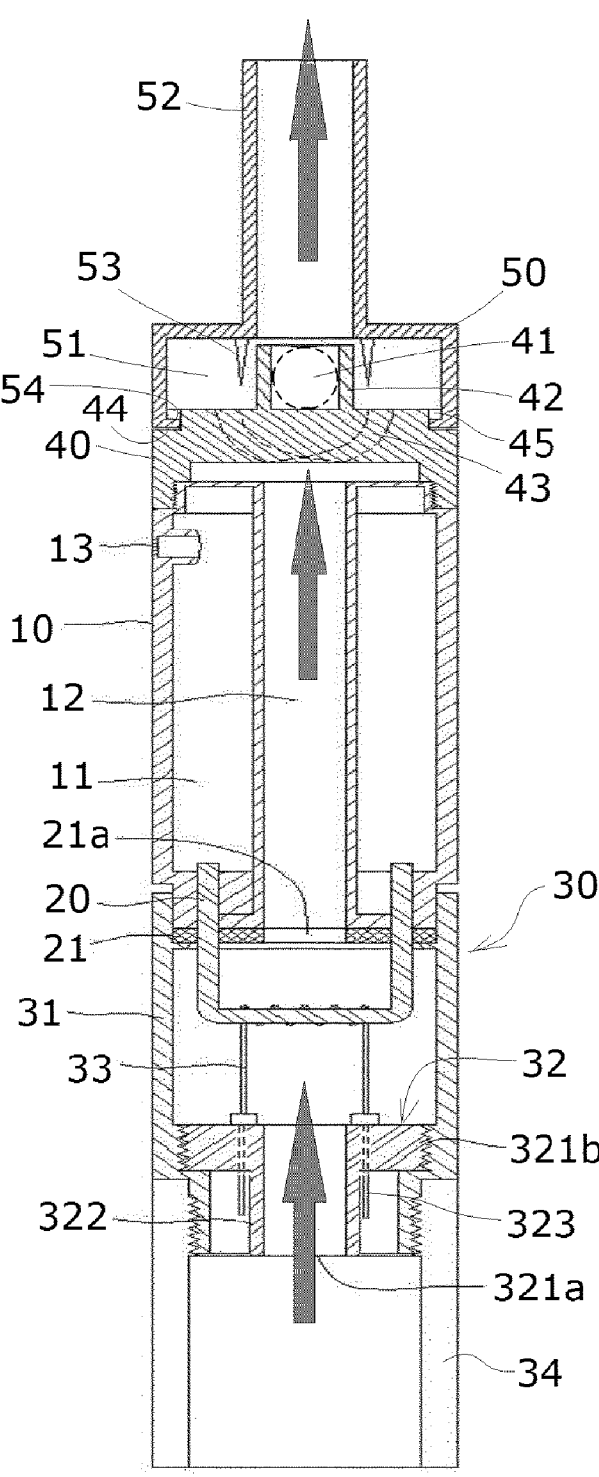
FIG. 2 is a sectional view showing the drug vaporization and inhalation device according to the first embodiment of the present invention.
Figure 3:
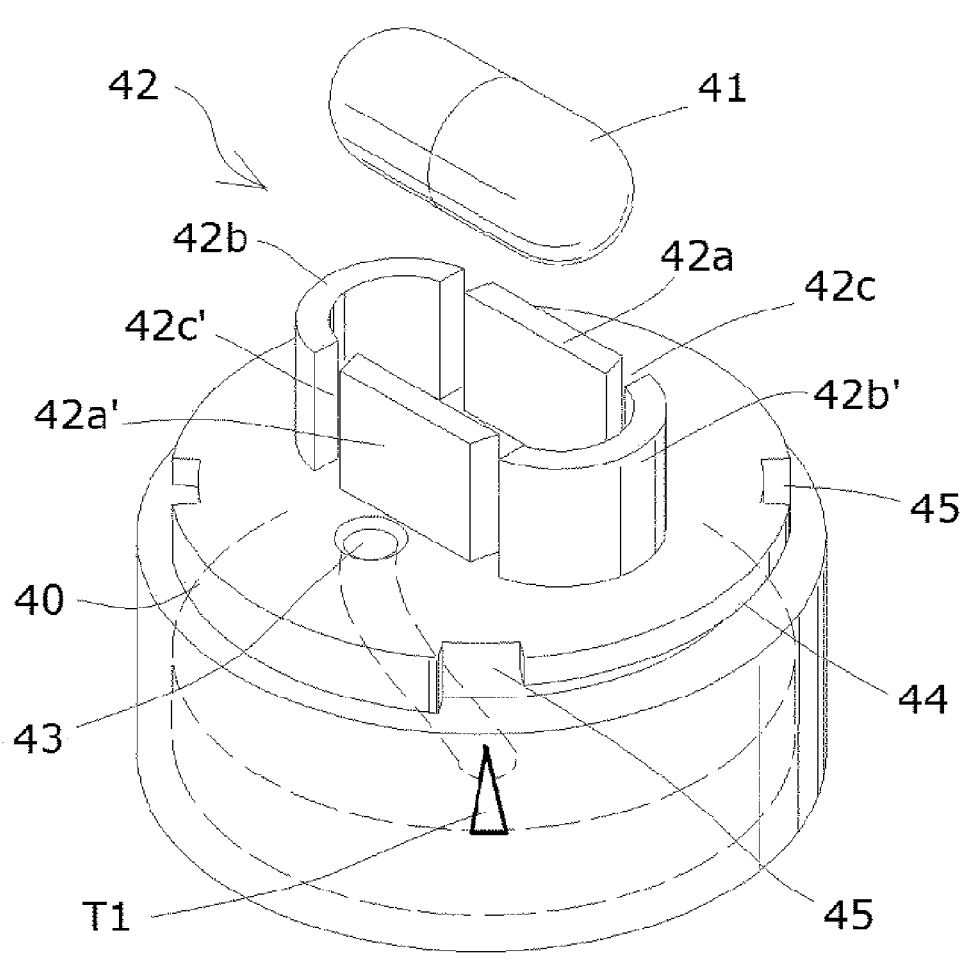
FIG. 3 is an enlarged perspective view showing a body of the drug vaporization and inhalation device according to the first embodiment of the present invention.

FIG. 1 is an exploded perspective view showing a drug vaporization and inhalation device according to a first embodiment of the present invention, FIG. 2 is a sectional view showing the drug vaporization and inhalation device according to the first embodiment of the present invention, and FIG. 3 is an enlarged perspective view showing a body of the drug vaporization and inhalation device according to the first embodiment of the present invention.

Figure 4:
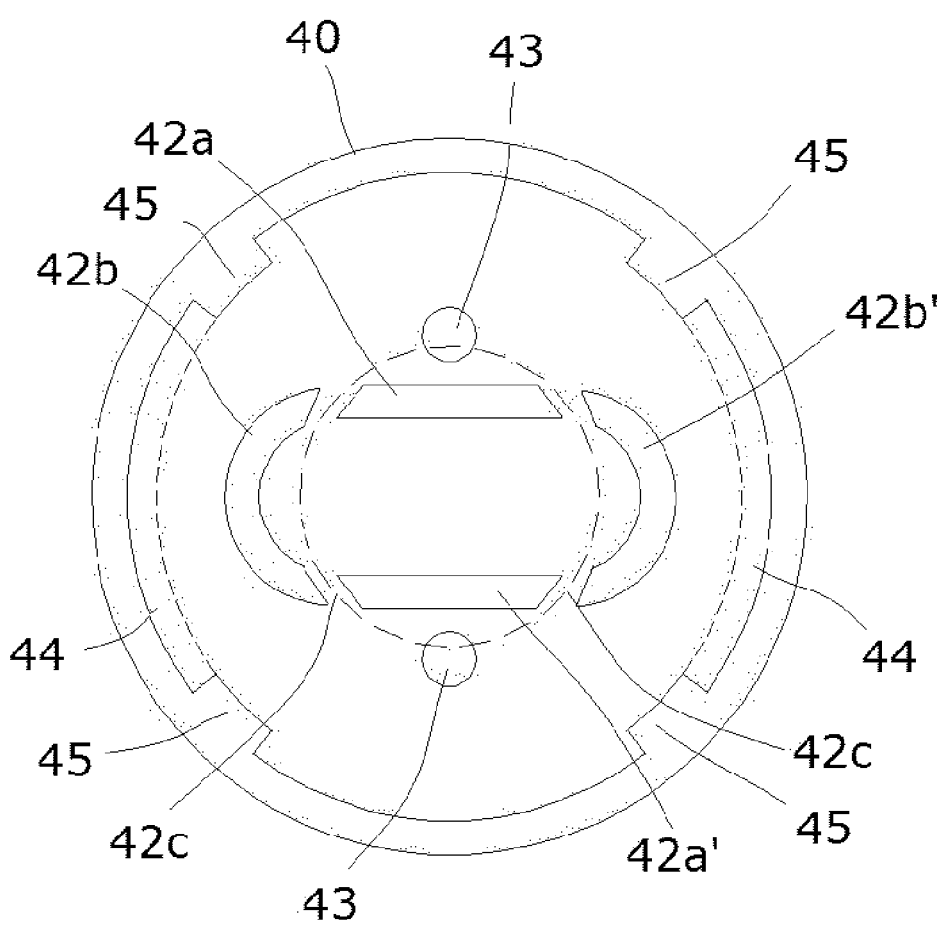
FIG. 4 is a schematic plan view showing the body of FIG. 3 according to the first embodiment of the present invention.
Figure 5:
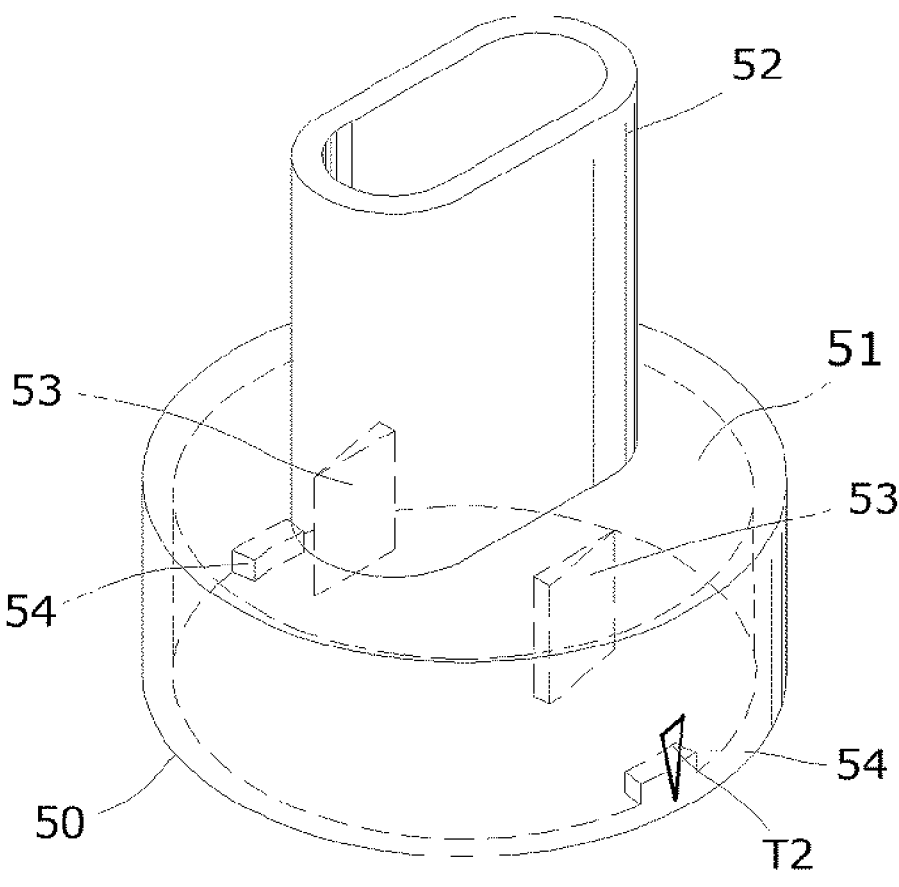
FIG. 5 is an enlarged perspective view showing a cap of the drug vaporization and inhalation device according to the first embodiment of the present invention.
Figure 6:
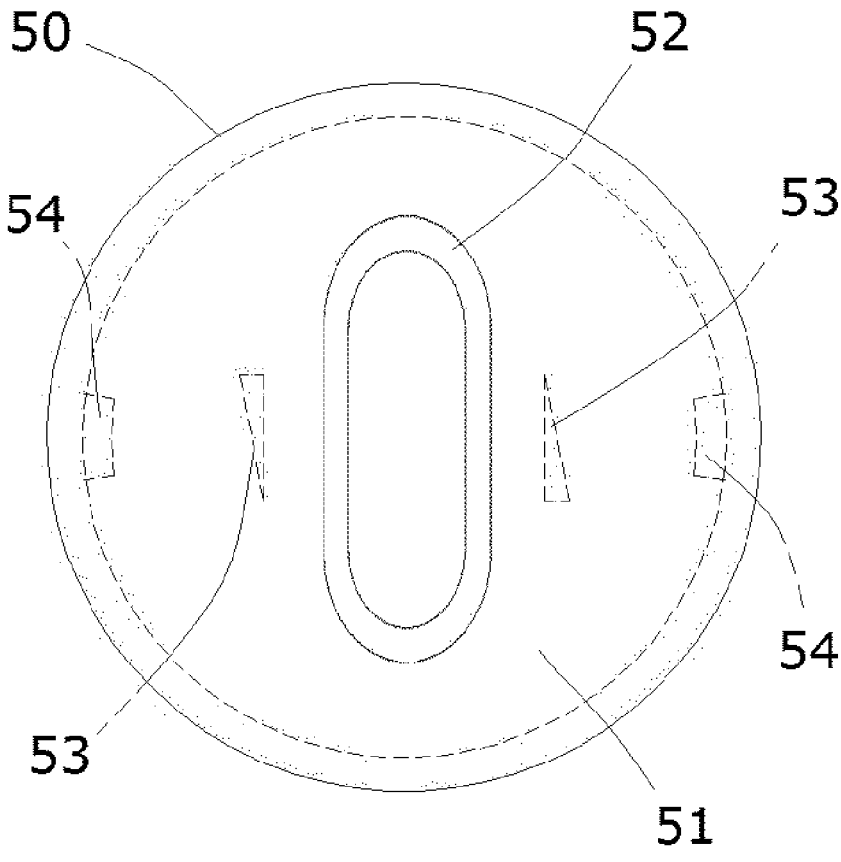
FIG. 6 is a schematic plan view showing the cap of FIG. 5 according to the first embodiment of the present invention.

FIG. 4 is a schematic plan view showing the body of FIG. 3 according to the first embodiment of the present invention, FIG. 5 is an enlarged perspective view showing a cap of the drug vaporization and inhalation device according to the first embodiment of the present invention, and FIG. 6 is a schematic plan view showing the cap of FIG. 5 according to the first embodiment of the present invention.

Referring to FIGS. 1 to 6, a drug vaporization and inhalation device according to a first embodiment of the present invention includes a vaporization container 10, an inducing material 20, a fine particle vaporizer 30, a body 40, and a cap 50.

The vaporization container 10 includes a first storage space 11 for storing a vaporization promoting composition and a first guide path 12 for discharging the steam generated when the vaporization promoting composition is vaporized by the fine particle vaporizer 30 to the body 40.

In this case, the vaporization container 10 has a liquid introducing valve 13 for introducing the vaporization promoting composition therethrough, and the first guide path 12 is definedly formed at the center of the vaporization container 10 or along the inner peripheral surface of the vaporization container 10.

That is, the vaporization container 10 is a hollow structure in which the first guide path 12 is built at the center thereof, and accordingly, one unitary chimney-like structure is formed around the first guide path 12.

In this case, the vaporization promoting composition includes any one of a general nutrient, a mineral, a vitamin, an amino acid, and a biostimulant, as elements having no harm to the human body.

The general nutrient includes any one selected from water, protein, lipid, carbohydrate, insoluble dietary fiber, soluble dietary fiber, total dietary fiber, and sugar, or a combination of any two or more thereof; the mineral includes any one selected from calcium, phosphorus, iron, sodium, magnesium, manganese, zinc, cobalt, copper, molybdenum, selenium, fluorine, iodine, and ash, or a combination of any two or more thereof; the vitamin includes any one selected from vitamin A, retinol (RE), β-carotene, thiamine, riboflavin, niacin, vitamin C, vitamin B6, pantothenic acid, vitamin B12, folate, vitamin D, vitamin E, and vitamin K, or a combination of any two or more thereof; the amino acid includes any one selected from isoleucine, leucine, lysine, methionine, cysteine, phenylalanine, tyrosine, threonine, tryptophan, valine, histidine, arginine, aspartic acid, glutamate, glycine, proline, and serine, or a combination of any two or more thereof; and the biostimulant includes any one selected from daidzein, genistein, glycitein, cyanidin, delphinidin, malvidin, pelargonidin, peonidin, petunidin, epicatechin, epicatechin 3-gallate, epigallocatechin, epigallocatechin 3-gallate, catechin, gallocatechin, eriodictyol, hesperitin, naringenin, apigenin, luteolin, isoharmnetin, kaempferol, myricetin, quercetin, monomer proanthocyanidin, dimer proanthocyanidin, trimer proanthocyanidin, 4-6 mers proanthocyanidin, 7-10 mers proanthocyanidin, polymer proanthocyanidin, choline, betanine, prokolin, glycerophosphocholine, phosphocholine, phosphatidylcholine, and sphingomyeline, or a combination of any two or more thereof.

Further, the vaporization promoting composition may include any one nutrient selected from an amino acid, gingko biloba, Co-Q10, Phosphatidyl Serine (PS), alpha lipoic acid, inorganic salts, and minerals; any one tea ingredient selected from green leaf, solomon's seal, Schisandra, Liriope platyphylla, corn silk, plum, tangerine skin, chrysanthemum, Acantheopanax albeofructus, quince, *Pueraria lobata*, goji berry, *Cornus officinalis*, Persimmon leaf, Eucommia ulmoides, oolong, and Chinese mallow; any one fruit ingredient selected from orange, lemon, and grapefruit; any one vegetable ingredient selected from a broccoli extract, a cabbage extract, onion, garlic, ginger, a lettuce extract, a kale extract, a *Platycodon grandiflorum* extract, and a tomato extract; any one oriental medicine ingredient selected from ginkgo leaves, Korean black raspberry, *Pueraria lobata*, Schisandra, *Torilis japonica, Cuscuta chinensis* Lam., *Cornus officinalis*, and *Senna tora*; and any one functional ingredient selected from royal jelly, plum, *Hovenia dulcis*, and xylitol, or a combination of two or more thereof.

The inducing material 20 is disposed under the vaporization container 10 to come into close contact therewith or to be inserted thereinto to induce the vaporization promoting composition stored in the first storage space 11 to be discharged by means of a capillary action, and in this case, the inducing material 20 is fixed to a fixing plate 21 having an air inlet hole 21*a* formed thereon to communicate with the first guide path 12, so that the internal space of the vaporization container 10 or the fine particle vaporizer 30 is divided into an inner space and an outer space.

In this case, the inducing material 20 is made of any one material of a multi-layered foamed nickel wire mesh, a stainless fiber felt, a polymer foaming agent, a metal porous material, and fibers, or a combination thereof.

In this case, the inducing material 20 comes into direct contact with the vaporization promoting composition stored in the first storage space 11 to thus shorten a moving path of the vaporization promoting composition, so that if the vaporization promoting composition has high viscosity, the inducing material 20 can prevent the moving speed of the vaporization promoting composition from being reduced owing to the high viscosity of the vaporization promoting composition.

The inducing material 20 has a given gap from the underside of the vaporization container 20 while being installed, and the gap may cause the vaporization promoting composition stored in the first storage space 11 to leak to the outside. Accordingly, the first storage space 11 accommodates fiber materials therein to prevent the vaporization promoting composition stored therein from leaking to the outside.

According to the embodiment of the present invention, further, the ends of the inducing material 20 are insertedly disposed into the underside of the vaporization container 10, but even though not shown in the drawings, according to another embodiment of the present invention, the ends of the inducing material 20 may come into close contact with the underside of the vaporization container 10 or bond to the underside of the vaporization container 10 in consideration of the leakage of the vaporization promoting composition. In this case, since the inducing material 20 is not insertedly disposed into the underside of the vaporization container 10, the vaporization container 10 may have communication holes formed on the underside thereof.

As a result, according to another embodiment of the present invention, the inducing material 20 comes into close contact with the communication holes, and accordingly, in a state where a diameter of the inducing material 20 is designed to be larger than that of each communication hole, the ends of the inducing material 20 are bonded to the outer peripheries of the communication holes by means of silicone. Otherwise, in a state where a diameter of the inducing material 20 is designed to be larger than that of each communication hole, the inducing material 20 is disposed on the communication holes by means of the application of a given pressure thereto, so that the vaporization promoting composition discharged through the communication holes is absorbed to the inducing material 20.

The fine particle vaporizer 30 is heated when power is supplied thereto to vaporize the vaporization promoting composition induced by the inducing material 20 and includes an atomizing container 31, an electrode part 32, a heating material 33, and a casing 34.

The atomizing container 31 is coupled to one end of the vaporization container 10 and has the other end coupled to the casing 34. Further, the atomizing container 31 accommodates the fixing plate 21 to which the inducing material 20 is fixed therein.

The electrode part 32 is coupled to the inside of the atomizing container 31 to supply the power to the heating material 33.

That is, the electrode part 32 includes an electrode body 321 having an inhalation hole 321a communicating with the first guide path 12 and a coupled screw portion 321b fixed to the bottom inner periphery of the atomizing container 31 whose both ends are open, while being electrically contacted with the atomizing container 31, and the electrode body 321 has a negative electrode 322 and a positive electrode 323 disposed on one side thereof to have electrical contacts with the heating material 33.

The heating material 33 is disposed on the outside surface of the inducing material 20 accommodated in the atomizing container 31 and thus heated by the power supplied from the electrode part 32 to vaporize the vaporization promoting composition induced by the inducing material 20.

In this case, the heating material 33 may be a heating filament wire having a coil structure made of a nickel alloy or a composition of rare earth elements, which is connected to the electrodes 322 and 323 and wound on the inducing material 20.

Otherwise, the heating material 33 may be a high frequency or very high frequency generator connected to the electrodes 322 and 323, and in this case, the inducing material 20 may be molded to the shape of a flat plate coming into close contact with the high frequency or very high frequency generator.

Otherwise, the heating material 33 may include peltier elements electrically connected to the electrodes 322 and 323 in parallel therewith, and in this case, absorber plates of the peltier elements may have physical contacts with the heating material 33.

In addition, the heating material 33 may be a heating filament wire having a coil structure made of a nickel alloy or a composition of rare earth elements, which is connected to the electrodes 322 and 323 and wound on the inducing material 20 and a high frequency or very high frequency generator connected to the electrodes 322 and 323, together. Otherwise, the heating material 33 may include peltier elements electrically connected to the electrodes 322 and 323 in parallel therewith, and in this case, absorber plates of the peltier elements may have physical contacts with the heating material 33.

Figure 7:
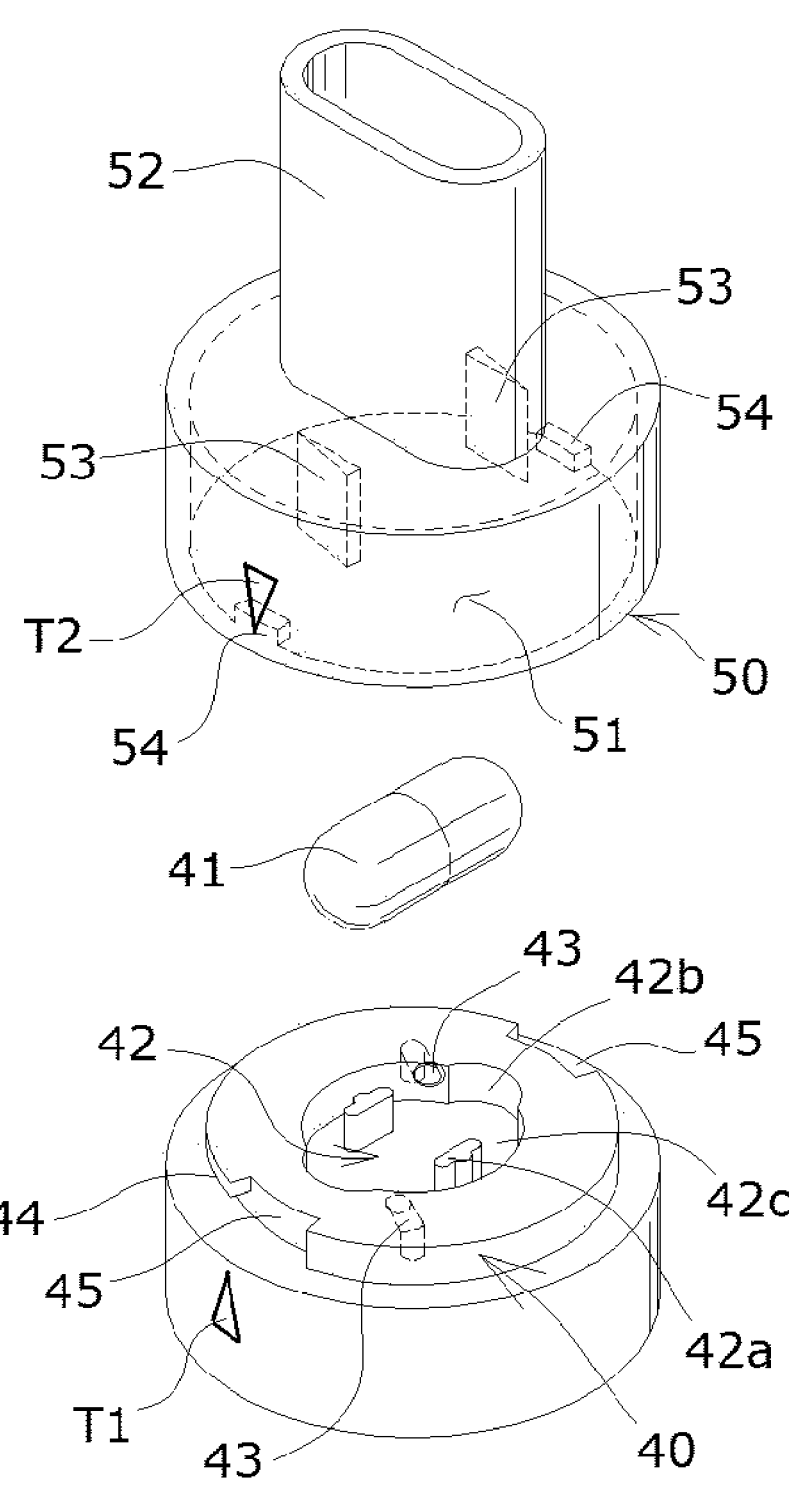
FIG. 7 is an enlarged perspective view showing a body of a drug vaporization and inhalation device according to a second embodiment of the present invention.
Figure 8A:
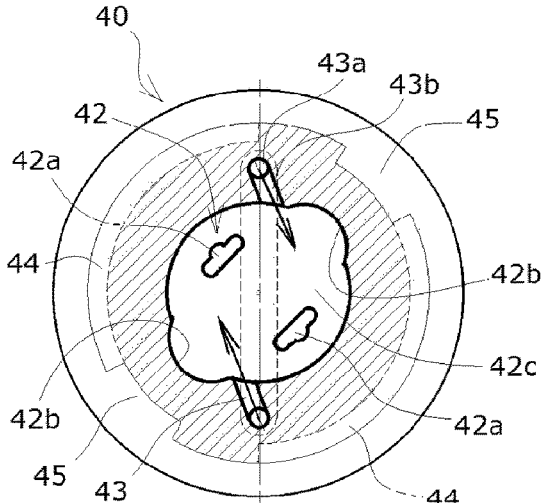
FIGS. 8A and 8B are schematic plan and bottom views showing the body of FIG. 7 according to the second embodiment of the present invention.
Figure 8B:
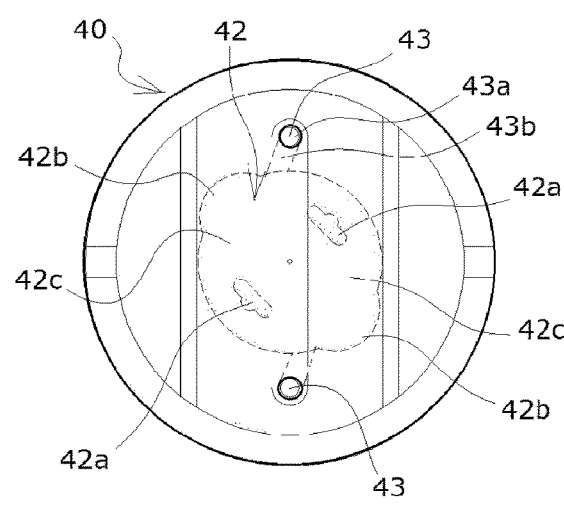

The body 40 is detachably coupled to top of the vaporization container 10 and has a capsule accommodation portion 42 protruding from top thereof, as shown in FIGS. 1 to 4 in the first embodiment of the present invention, or concavely formed on top thereof, as shown in FIGS. 7 to 8B in the second embodiment of the present invention, for accommodating a capsule 41 in which a powdered drug for an infected patient with asthma, a coronavirus, or the like is sealedly stored, and second guide paths 43 for steam discharge formed thereon to pass through the interior thereof in an up and down direction and thus communicate with the first guide path 12. The second guide paths 43 are located at the outside from the capsule 41 in which the powdered drug for the infected patient with asthma, a coronavirus, or the like is sealedly stored.

Moreover, the body 40 has rail grooves 44 formed on top outer periphery thereof to guide the rotation of the cap 50 and protrusion insertion slots 45 formed on both ends of each rail groove 44.

The capsule accommodation portion 42 according to the first embodiment of the present invention is illustrated in FIGS. 1 to 6. The capsule accommodation portion 42 protruding from top of the body 40 includes a pair of plate-shaped first wall members 42a and 42a' for supporting left and right walls of the capsule 41 and a pair of arch-shaped second wall members 42b and 42b' facingly spaced apart from each other in different directions from the pair of first wall members 42a and 42a' to support both ends of the capsule 41, so that a space for accommodating the capsule 41 is formed.

Further, the capsule accommodation portion 42 includes blade moving paths 42c formed in spaces between the plate-shaped first wall members 42a and 42a' and the arch-shaped second wall members 42b and 42b' to ensure spaces through which blades 53 as will be discussed later pass to incise one surface of the top of the capsule 41 when the cap 50 rotates.

The capsule accommodation portion 42 according to the second embodiment of the present invention is illustrated in FIGS. 7 to 8B. FIG. 7 is an enlarged perspective view showing a body of a drug vaporization and inhalation device according to the second embodiment of the present invention, and FIGS. 8A and 8B are schematic plan and bottom views showing the body of FIG. 7 according to the second embodiment of the present invention.

The capsule accommodation portion 42 according to the second embodiment of the present invention is concavely formed on top of the body 40 and includes a pair of plate-shaped first wall members 42a for supporting left and right walls of the capsule 41, a pair of arch-shaped second wall members 42b facingly spaced apart from each other in different directions from the pair of first wall members 42a and 42a' to support both ends of the capsule 41, and blade moving paths 42c formed in spaces between the plate-shaped 42a and the arch-shaped second wall members 42b to ensure spaces through which the blades 53 pass to incise one surface of the top of the capsule 41 when the cap 50 rotates.

The cap 50 is rotatably coupled to top of the body 40 and has a mixing space 51 formed on the inner bottom thereof to face the capsule accommodation portion 42 formed on top of the body 40.

The cap 50 further includes an inhalation pipe 52 for the infected patient with asthma, a coronavirus, or the like that extends upward from the center thereof to pass therethrough in an up and down direction thereof and the blades 53 protruding downward from the inner bottom thereof to partially incise the surface of the capsule 41 placed in the capsule accommodation portion 42.

When the cap 50 rotates, the blades 53 for the incision of the surface of the capsule 41 pass through the blade moving paths 42c formed in spaces between the plate-shaped first wall members 42a and the arch-shaped second wall members 42b disposed in the capsule accommodation portion 42 formed on top of the body 40 and thus incise one side of top of the capsule 41 placed in the capsule accommodation portion 42 to discharge the powdered drug from the capsule 41.

Further, the body 40 includes second guide paths 43 formed at the outside of the capsule accommodation portion 42 formed on top thereof to discharge the vaporized steam to the capsule 41 accommodatedly fixed to the plate-shaped first wall members 42a and the arch-shaped second wall members 42b.

In this case, the second guide paths 43 pass through the body 40 in an up and down direction of the body 40 and serve to discharge the vaporized steam induced through the first guide path 12 to the capsule 41, and accordingly, the powdered drug discharged from the capsule 41 whose top one side is incised by means of the blades 53 is contained in the vaporized steam and is then inhaled through the inhalation pipe 52.

The second guide paths 43 desirably generate a vortex in the mixing space 51 provided between the cap 50 and the body 40 when the vaporized steam is discharged to the capsule 41 placed between the body 40 and the cap 50, and if the second guide paths 43 pass through the body 40 in the up and down direction of the body 40 as shown in FIGS. 1 to 6 according to the first embodiment of the present invention, they may be desirably twistedly formed.

In the case of the second guide paths 42 according to the second embodiment of the present invention, as shown in FIGS. 7 to 8B, the capsule accommodation portion 42 is concavely formed in the body 40, and accordingly, each second guide path 42 includes a vertical path 43a extending vertically from the bottom of the body 40 and a horizontal path 43b extending horizontally from the vertical path 43a and having an outlet open toward the inner peripheral surface of the capsule accommodation portion 42, so that the second guide path 42 provides a connection path having a generally "¬"-shaped sectional area.

In this case, the horizontal path 43b open toward the inner peripheral surface of the capsule accommodation portion 42 is kept to an inclination of 15 to 45° toward one side of the body 40 from the center of the body 40, so that the vaporized steam discharged from the second guide paths 43 through the first guide path 12 is positioned toward one side of top of the capsule 41 incised by the blades 53 and simultaneously, the powdered drug separated from the incised surface of the capsule 41 owing to the discharge pressure of the vaporized steam in both of the up and down directions is rotatingly mixed with the vaporized steam, thereby generating a vortex in the mixing space 51 provided between the cap 50 and the body 40.

That is, the outlets of the second guide paths 43 are positioned toward the blade moving paths 42c formed in the spaces between the first wall members 42a and the second wall members 42b in the capsule accommodation portion 42.

As a result, the vaporized steam discharged to the capsule 41 comes into direct contact with the powdered drug discharged from the capsule 41 whose top one side is incised by means of the blades 53, thereby optimizing the powdered drug mixing efficiency.

The cap 50 further includes locking protrusions 54 formed on the inner periphery thereof, seated on the protrusion insertion slots 45, and thus rotating along the rail grooves 44. Further, the body 40 has a first mark T1 formed on the outer peripheral surface thereof and the cap 50 has a second mark T2 formed on the outer peripheral surface that correspond to one side locking protrusion 54.

The first and second marks T1 and T2 serve to guide a position where only the vaporized steam induced through the first guide path 12 is selectedly discharged through the inhalation pipe 52 or a position where the powdered drug discharged from the capsule 41 is mixedly contained in the vaporized steam and thus discharged, without any damage on the capsule 41 located inside the capsule accommodation portion 42, according to the rotating range of the cap 50.

As shown in FIGS. 1 to 8B, the drug vaporization and inhalation device according to the embodiments of the present invention operates by opening the liquid introducing valve 13 of the vaporization container 10 to allow the first storage space 11 of the vaporization container 10 to be filled with the vaporization promoting composition.

Next, the capsule 41 in which the fine particle powdered drug is sealedly stored is seated in the capsule accommodation portion 42 of the body 40, and the body 40 is screw-coupled to top of the vaporization container 10. Further, the cap 50 is coupled to top of the body 40.

After that, if power is applied to the fine particle vaporizer 30 located at one end of the vaporization container 10, the power is supplied to the heating material 33 through the electrode part 32 in the fine particle vaporizer 30, and accordingly, the heating material 33 vaporizes the vaporization promoting composition induced by the inducing material 20 to generate vaporized steam, so that the vaporized steam passes through the air inlet hole 21a of the fixing plate 21 to which the inducing material 20 is fixed and the first guide path 12 of the vaporization container 10 and is then discharged to the second guide paths 43 formed on the body 40.

In this case, if the infected patient with asthma, a coronavirus, or the like desires to inhale only the vaporized steam discharged to the second guide paths 43, he or she minimizes the rotation of the cap 50, while watching the first and second marks T1 and T2 formed on the outer peripheral surfaces of the body 40 and the cap 50.

That is, when the locking protrusions 54 of the cap 50 rotate along the rail grooves 44 after seating onto one side protrusion slots 45 of the body 40, the rotation of the cap 50 is minimized to prevent the locking protrusions 54 from passing through the blade moving paths 42c formed on the capsule accommodation portion 42.

As a result, the capsule 41 seatedly placed in the capsule accommodation portion 42 is not incised by means of the blades 53 mounted on the cap 50, thereby preventing the powdered drug from being discharged from the capsule 41, and accordingly, if the infected patient with asthma, a coronavirus, or the like holds the inhalation pipe 52 in his or her mouth and breathes, only the vaporized steam reaches his or her lungs through the second guide paths 43.

However, if the infected patient with asthma, a coronavirus, or the like desires to mix the vaporized steam discharged to the second guide paths 43 with the powdered drug of the capsule 41 and to inhale the vaporized steam mixed with the powdered drug, he or she increases the rotation of the cap 50, while watching the first and second marks T1 and T2 formed on the outer peripheral surfaces of the body 40 and the cap 50.

That is, when the locking protrusions 54 of the cap 50 rotate along the rail grooves 44 after seating onto one side protrusion slots 45 of the body 40, the rotation of the cap 50 is increased to allow the locking protrusions 54 to pass through the blade moving paths 42c formed on the capsule accommodation portion 42 and to then seated onto the other side protrusion slots 45.

As a result, the capsule 41 seatedly placed in the capsule accommodation portion 42 is incised by means of the blades 53 mounted on the cap 50, thereby causing the powdered drug sealedly stored in the capsule 41 to be discharged from the capsule 41, and accordingly, if he or she holds the inhalation pipe 52 in his or her mouth and breathes, the powdered drug is mixed with the vaporized steam discharged to the mixing space 51 through the second guide paths 43. As a result, the powdered drug mixed with the vaporized steam reaches his or her lungs through the inhalation pipe 52, without any loss.

That is, if the infected patient with asthma, a coronavirus, or the like inhales the powdered drug discharged from the capsule 41 through the inhalation pipe 52, the powdered drug is mixed with the vaporized steam discharged from the mixing space 51 through the second guide paths 43, and the vaporized steam mixed with the powdered drug transfers the powdered drug to the lungs of the infected patient with asthma, a coronavirus, or the like.

INDUSTRIAL APPLICABILITY

As described above, the drug vaporization and inhalation device according to the exemplary embodiments of the present invention has been described with reference to the attached drawings, but the drug vaporization and inhalation device is not limited by the exemplary embodiments of the present invention.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A drug vaporization and inhalation device comprising:
a vaporization container having a first storage space for storing a vaporization promoting composition and a first guide path for discharging steam;
an inducing material disposed under the vaporization container to be inserted into the first storage space, the inducing material comprising a porous member configured to draw, by capillary action, the vaporization promoting composition stored in the first storage space;
a fine particle vaporizer heated when power is supplied thereto to vaporize the vaporization promoting composition induced by the inducing material;
a body detachably coupled to top of the vaporization container and having a capsule accommodation portion formed on top thereof to accommodate a capsule in which a powdered drug for a user is sealedly stored and second guide paths for steam discharge formed in the body to pass through an interior of the body in an up and down direction of the body, communicate with the first guide path, and discharge the vaporized steam induced from the fine particle vaporizer to the capsule located inside the capsule accommodation portion; and
a cap rotatably coupled to the top of the body and having a mixing space formed on the inner bottom thereof, an inhalation pipe for the user communicating with the mixing space, and blades protruding downward from the inner bottom thereof to incise the capsule placed in the capsule accommodation portion, so that the vaporized steam or the powdered drug discharged from the capsule and mixed with the vaporized steam guided by the second guide paths is configured to be inhaled by the user through the inhalation pipe,
wherein the body, which is coupled to the top of the vaporization container, comprises rail grooves formed on top outer periphery thereof to guide the rotation of the cap and protrusion insertion slots formed on both ends of each rail groove.

2. The drug vaporization and inhalation device according to claim 1, wherein the blades protrude downward from the inner bottom of the cap, and the cap has locking protrusions formed on an inner periphery thereof, the locking protrusions being configured to seat on the protrusion insertion slots of the body and to rotate along the rail grooves.

3. The drug vaporization and inhalation device according to claim 2, wherein the body has a first mark formed on an outer peripheral surface of the body corresponding to one of the protrusion insertion slots and the cap has a second mark formed on an outer peripheral surface of the cap corresponding to one of the locking protrusions, so as to guide a position where the vaporized steam is discharged through the inhalation pipe or a position where the powdered drug discharged from the capsule is mixedly contained in the vaporized steam and thus discharged.

4. The drug vaporization and inhalation device according to claim 1, wherein the second guide paths have "L"-shaped paths extending from a bottom surface of the body to an inner peripheral surface of the capsule accommodation portion, and inner outlets of the paths are close to blade moving paths formed in spaces between first wall members and second wall members.

5. The drug vaporization and inhalation device according to claim 4, wherein each second guide path provides a connection path having a generally "L"-shaped sectional area by means of a vertical path extending vertically from the bottom of the body and a horizontal path extending horizontally from the vertical path and having an outlet open toward the inner peripheral surface of the capsule accommodation portion.

6. The drug vaporization and inhalation device according to claim 5, wherein the horizontal path open toward the inner peripheral surface of the capsule accommodation portion is kept to an inclination of 15 to 45° toward one side of the body from a center of the body, so that the vaporized steam discharged from the second guide paths through the first guide path is positioned toward one side of top of the capsule incised by the blades, and simultaneously, a vortex in the mixing space is generated.

7. The drug vaporization and inhalation device according to claim 1, wherein each second guide path provides a connection path having a generally "L"-shaped sectional area by means of a vertical path extending vertically from a bottom of the body and a horizontal path extending horizontally from the vertical path and having an outlet open toward an inner peripheral surface of the capsule accommodation portion.

8. The drug vaporization and inhalation device according to claim 7, wherein the horizontal path open toward the inner peripheral surface of the capsule accommodation portion is kept to an inclination of 15 to 45° toward one side of the body from a center of the body, so that the vaporized steam discharged from the second guide paths through the first guide path is positioned toward one side of top of the capsule incised by the blades, and simultaneously, a vortex in the mixing space is generated.

9. The drug vaporization and inhalation device according to claim 1, wherein the vaporization container has a liquid introducing valve for introducing the vaporization promoting composition therethrough.

10. The drug vaporization and inhalation device according to claim 1, wherein the first guide path is formed at a center of the vaporization container or formed along an inner peripheral surface of the vaporization container.

11. The drug vaporization and inhalation device according to claim 1, wherein the inducing material is fixed to a fixing plate having an air inlet hole formed thereon, so that the internal space of the vaporization container or the fine particle vaporizer is divided into an inner space and an outer space.

12. The drug vaporization and inhalation device according to claim 11, wherein the inducing material is made of any one material of a multi-layered foamed nickel wire mesh, a stainless fiber felt, a polymer foaming agent, a metal porous material, and fibers, or a combination thereof.

13. The drug vaporization and inhalation device according to claim 11, wherein the fine particle vaporizer comprises:

an atomizing container coupled to one end of the vaporization container to accommodate the fixing plate to which the inducing material is fixed therein;

an electrode part screw-coupled to the inside of the atomizing container; and a heating material disposed on the outside surface of the inducing material accommodated in the atomizing container and thus heated by the power supplied from the electrode part to vaporize the vaporization promoting composition induced by the inducing material.

14. The drug vaporization and inhalation device according to claim 13, wherein the electrode part comprises:

an electrode body having an inhalation hole communicating with the first guide path and a coupled screw portion fixed to a bottom inner periphery of the atomizing container, the atomizing container having both ends open, while being electrically contacted with the atomizing container;

a negative electrode disposed on one side of the electrode body to have the electrical contact with the heating material; and a positive electrode disposed on one side of the electrode body to have the electrical contact with the heating material.

15. The drug vaporization and inhalation device according to claim 14, wherein the heating material comprises at least one of:

a heating filament wire having a coil structure made of a nickel alloy or a composition of rare earth elements, which is connected to the electrodes and wound on the inducing material;

frequency generator connected to the electrodes so that the inducing material is molded to a shape of a flat plate coming into close contact with the frequency generator; and peltier elements electrically connected to the electrodes in parallel therewith so that absorber plates of the peltier elements have physical contacts with the heating material.

16. The drug vaporization and inhalation device according to claim 1, wherein the vaporization promoting composition comprises any one of a general nutrient, a mineral, a vitamin, an amino acid, and a biostimulant.

* * * * *